United States Patent [19]

Barrere et al.

[11] Patent Number: 4,684,613

[45] Date of Patent: Aug. 4, 1987

[54] DEVICE FOR CARRYING OUT WITHDRAWALS OF SAMPLES FROM SEMI-SOLID MEDIA

[75] Inventors: Genevieve C. Barrere; Marie-élène H. Beydon, both of Paris; Lionel Drugeault, Charenton; Jean-Pierre Vasseur, Longjumeau, all of France

[73] Assignee: Rhone-Poulenc Sante, Courbevoie, France

[21] Appl. No.: 724,889

[22] Filed: Apr. 19, 1985

[30] Foreign Application Priority Data

Apr. 19, 1984 [FR] France .................................. 84 06203

[51] Int. Cl.⁴ .......................... C12M 1/20; C12M 1/26
[52] U.S. Cl. .................................... 435/301; 435/293; 435/287; 83/98; 83/100
[58] Field of Search ............... 435/292, 293, 294, 299, 435/300, 301; 83/98, 99, 100; 414/416, 744 B

[56] References Cited

U.S. PATENT DOCUMENTS

| | | | |
|---|---|---|---|
| 1,372,949 | 3/1921 | Henneberry | 83/99 |
| 2,182,744 | 12/1939 | Ehrsam | 83/100 X |
| 2,463,455 | 3/1949 | Dann | 83/100 X |
| 2,982,699 | 5/1961 | Johnson et al. | 435/292 |
| 3,227,522 | 1/1966 | Salisbury, Jr. et al. | 435/301 X |
| 3,240,851 | 3/1966 | Scalora | 83/99 X |
| 3,482,478 | 12/1969 | Einhorn | 83/100 |
| 3,765,542 | 10/1973 | White | 414/416 X |
| 4,221,533 | 9/1980 | Heim et al. | 414/744 B |
| 4,341,735 | 7/1982 | Seifried | 435/292 X |

Primary Examiner—Alan Cohan
Assistant Examiner—John A. Rivell
Attorney, Agent, or Firm—Stevens, Davis, Miller & Mosher

[57] ABSTRACT

A device for automatically carrying out the withdrawal and deposition of core samples of semi-solid media in which one or more hollow punches are mounted for movement in three mutually perpendicular directions, so that the punch can be brought above and lowered into the media, a vacuum applied to suck the media into a chamber in the punch, the punch then being raised and moved to a position above a second media, the vacuum then being removed and compressed air applied after the punch has been lowered over the other media, thereby to push the sample removed from the first media from the punch. The operations can all be controlled automatically.

5 Claims, 19 Drawing Figures

DEVICE FOR CARRYING OUT WITHDRAWALS OF SAMPLES FROM SEMI-SOLID MEDIA

The present invention relates to an automatic device for withdrawing a core sample from a semi-solid medium and depositing it on another medium while preserving its characteristics.

The device according to the invention is especially useful for carrying out withdrawals of samples from agar culture media used in microbiology, and in particular for carrying out the A.P.M. method (Agar Piece Method) described, for example, by T. Ichikawa et al., Folia Microbiol., 16, 218 (1971).

The A.P.M. technique consists in withdrawing, with the aid of a calibrated hollow punch, a cylindrical core sample from an agar nutrient medium on which a microorganism is growing. This agar cylinder is then deposited on another semi-solid medium which enables the presence of an active product in the cylinder to be detected, and possibly to be assayed. The active product can be: either a metabolite (a) or an antimetabolite (b) synthesised by the microorganism, the demonstration of which can be carried out by microbiological and/or enzymatic and/or chemical methods. For example, in the case of microbiological demonstration, the agar medium for demonstration can contain a test microorganism which requires the presence of a metabolite (a) for its growth, or which is sensitive to the antimetabolite (b) studied. After incubation, one can either study the diameter of the rings in which growth of the test microorganism is exhibited or inhibited and this provides information about the amount of active product present in the agar core, or one can study a component of the culture medium, where it is desired to follow the changes occurring during the growth of the microorganism, for example a carbon-containing substrate, a nitrogenous substrate or a metabolite effecting the biosynthesis of the product studied (precursor, regulation factor, or antimetabolite). As above, the demonstration can be carried out by a microbiological, enzymatic or chemical method.

The A.P.M. method is especially useful, for example, for selecting microbial strains (improvement in productivity, improvement in the quality of a specified active substance) or for detecting new activities.

Hitherto, the devices used in the laboratory for carrying out the A.P.M. method are manual hollow punches equipped with a coaxial drift. The hollow punch is a hollow cylinder, the internal diameter of which is, e.g., 4 mm and the external diameter 6 mm, and the end of which is bevelled outwards. Withdrawal of the sample is effected by cutting out the core with the aid of the hollow punch, then performing a tilting movement to detach the core from the bottom of the dish, and then lifting the hollow punch. The core sample thus withdrawn is then deposited on the surface of another suitable agar medium by expelling it with the aid of the drift, the diameter of which is slightly less than the internal diameter of the hollow punch so that it can slide easily. Using such a device, the core samples obtained are not reproducible in shape, which varies with the approach angle at the time of cutting out the sample.

It is especially useful to be able to automate as far as possible the A.P.M. method, to improve reproducibility and to accomplish a large number of manipulations rapidly, which is especially desirable for the efficient selection of strains.

According to the present invention, we provide a device for automatically carrying out the withdrawal and deposition of core samples of semi-solid media, said device comprising:

(a) a carrier;
(b) means mounting said carrier for reciprocable movement in three mutually perpendicular directions,
(c) a holder mounted on said carrier;
(d) at least one hollow punch mounted on said holder, said at least one punch defining, in its interior, a punch chamber having a lower cutting edge;
(e) a bore through said punch, communicating with said chamber, the diameter of said bore being less than the diameter of said chamber;
(f) a compressed air source;
(g) a vacuum generator;
(h) means selectively connecting said bore to said compressed air source or said vacuum generator; and
(i) control means governing the movement of said carrier and of said selective connecting means.

In order that the present invention may be more readily understood, the following description is given, merely by way of example, reference being made to the accompanying drawings in which.

Figure 4A:
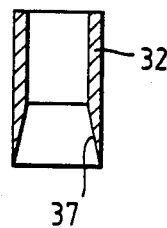
Figure 4B:
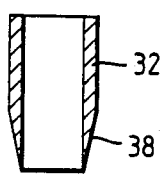
Figure 4C:
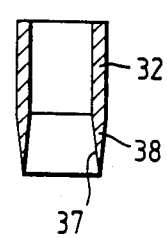
Figure 4D:
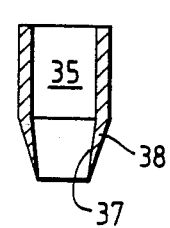
Figure 4E:
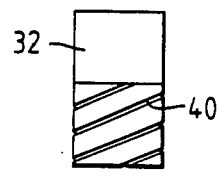
Figure 4F:
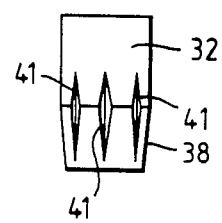
Figure 5:
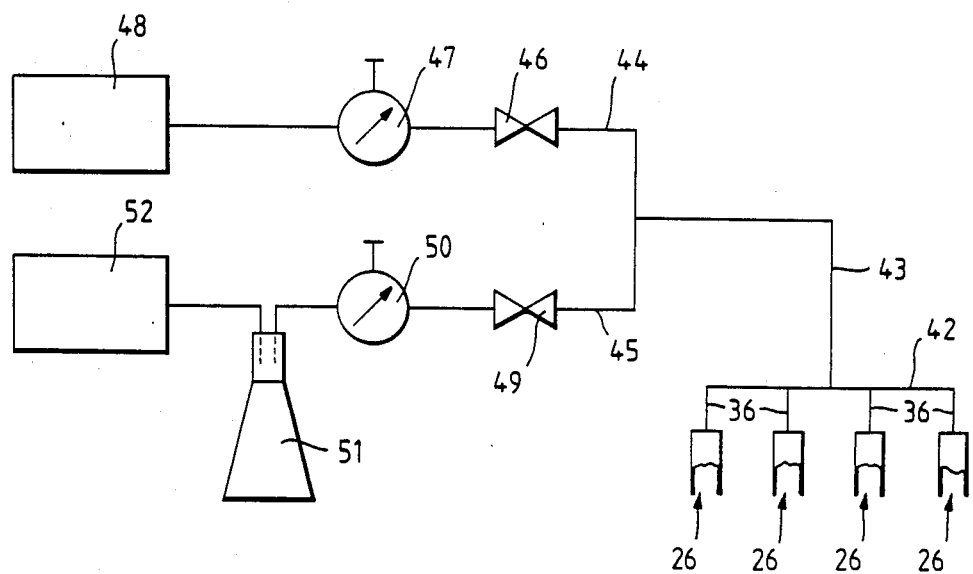
Figure 6:
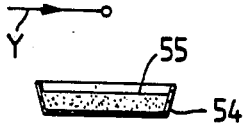
Figure 6:
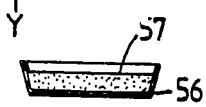
Figure 6:
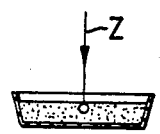
Figure 6:
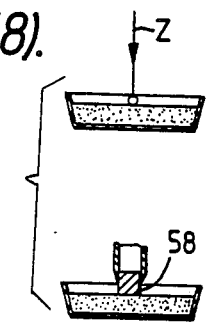
Figure 6:
Figure 6:
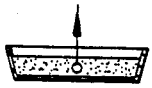
Figure 6:
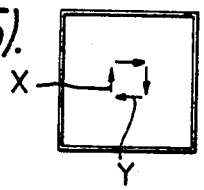
Figure 6:
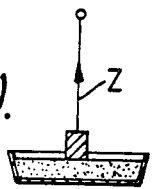
Figure 6:
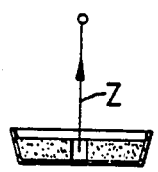

FIGS. 4 A to F show six embodiments of punch tip;

FIG. 5 is a schematic view of the control system of the device of FIGS. 1 to 4; and FIGS. 6 (1) and 6 (6) are schematic views showing the lifting of the sample and FIGS. 6 (7) to 6 (9) show the deposition of the lifted sample.

Figure 1:
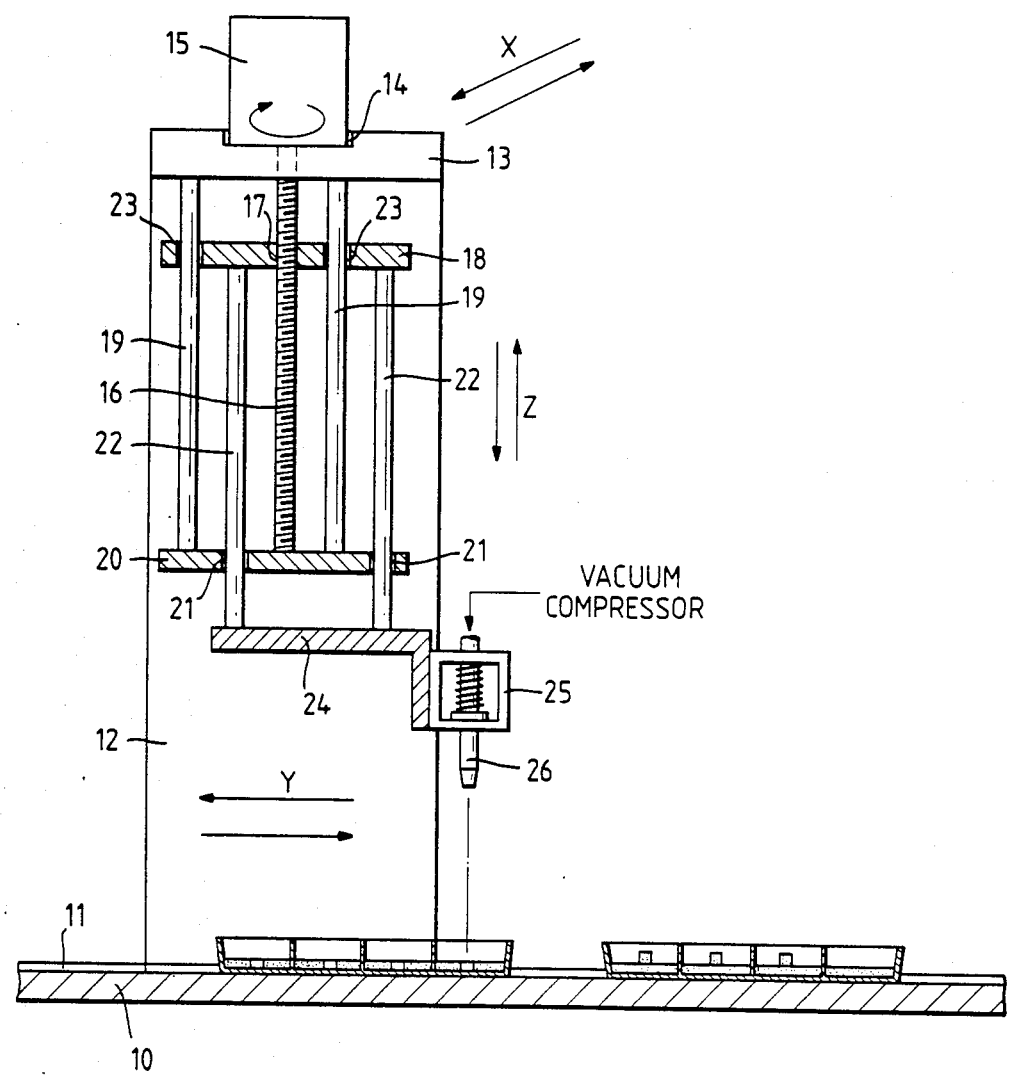
FIG. 1 is a schematic side elevation, partly in section, of one embodiment of device according to the present invention.

Referring first to FIG. 1, there is illustrated a base 10 having a guideway 11 along which is slidable a frame 12 in the direction of the arrows Y. The frame 12 has an upper member 13 including a guideway 14 perpendicular to the guideway 11 and on this guideway is mounted, for sliding movement in a direction perpendicular to the arrows Y, (as illustrated schematically by arrows X), a motor assembly 15. This has a vertically downwardly extending threaded shaft 16 which passes through a threaded aperture 17 in an upper plate 18. Extending vertically downwardly from member 13 are two columns 19 which carry a lower plate 20 provided with slots 21 therein through which pass vertical shafts 22 extending downwardly from the upper plate 18. The columns 19 pass through slots 23 in the upper plate 18.

Figure 2:
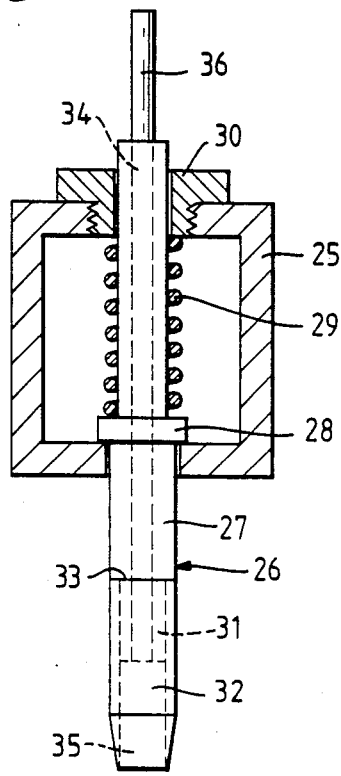
FIG. 2 is an enlarged cross-sectional view through a punch holder and illustrating one form of punch.
Figure 3:
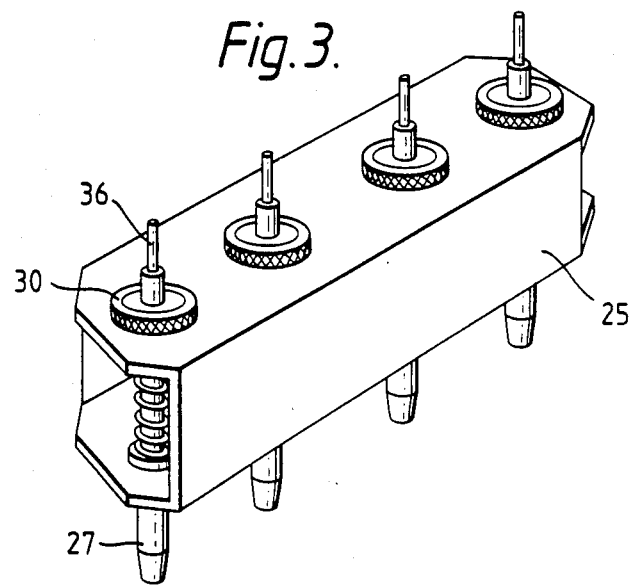
FIG. 3 is a perspective view of a punch holder of the device of FIG. 1 shown with four punches mounted thereon.

Supported to the lower ends of the shafts 22 is a carrier 24 on which is mounted a holder 25 (see also FIGS. 2 and 3).

The arrangement of the slides 11 and 14 and of the motor 15 and threaded shaft 16 are such as to enable the carrier 24, and with it the holder 25, to move in the Y direction, the X direction and the vertical Z direction in a reciprocably manner in each case. Thus the holder can move in three mutually perpendicular directions.

Supported in the holder are one or more (four as shown in FIG. 3) punches 26 and these punches include a main body 27 having a radial flange 28 thereon against which abuts a helical compression spring 29 the upper end of which is engaged by a nut 30 screwed into the upper part of the holder 25. This allows limited vertical movement of the punch 26 against the action of the spring 29.

The body 27 includes a spigot 31 over which can be fitted a hollow punch member 32, the upper end of which engages a shoulder 33 at the upper end of the spigot 31. The body 27 and the spigot 31 are provided with an axial bore 34 communicating at the lower end with the space 35 formed within the punch member 32 and at the upper end with a flexible pipe 36.

Various forms of punch member 32 are illustrated in FIG. 4. In FIG. 4A the lower end of the punch is provided with an internal bevel 37 and in FIG. 4B (and in FIG. 2) it is shown with an external bevel 38. FIG. 4C illustrates an internal bevel 37 together with an external bevel 38 while FIG. 4D shows an external bevel 38 and an internal taper extending downwardly from the chamber 35.

FIG. 4E shows the lower part of the punch member 32 provided with one or more helical grooves 40 while in FIG. 4F there is an external bevel 38 and a plurality of generally axially extending grooves 41.

FIG. 5 illustrates schematically how the various punches are connected to a source of compressed air and a source of vacuum. There are illustrated on the right of FIG. 5 four punches 26 with their four pipes 36 connected via a manifold 42 to a tube 43 which divides to form two tubes 44 and 45. Tube 44 is connected via an electromagnetic valve 46 and a manometer 47 to a source of compressed air illustrated as a block 48. Similarly the tube 45 is connected via an electromagnetic valve 49, a manometer 50, a collection vessel 51 to a vacuum source illustrated schematically at 52.

The operation of the apparatus is shown diagramatically in FIG. 6. In this figure (and in FIG. 1), there is shown a Petri dish 54 which is filled with agar 55 from which a sample is to be taken. A control device (not shown) moves the holder 25 in the direction of the arrow Y, see FIG. 6 (1) and then in the direction of the arrow Z (see FIG. 6 (2)). The lower tip of the punch or punches 26 will engage the upper surface of the agar, initially, and will then move downwardly. When the lower surface engages the bottom of the dish, there will be a slight compression of the spring 29. The provision of the bevel or bevels 37 to 39 and/or of the grooves 40, 41, assists in allowing air to reach the bottom of the vessel, thereby releasing any suction effect of the slug of agar which has been introduced into the cavity 35 of the or each punch. This situation can be improved by moving the carrier 24 and thus the holder 25 and the punch or punches 26 in both the X and Y direction by a small amount, e.g. 2 mm, as illustrated in FIG. 6 (5). At this stage the valve 49 is opened and a vacuum is applied via the flexible tubes 43 and the manifold 42 to the pipes 36 and thus to the bore 34 and the interior upper portion of the cavity or cavities 35. Once the suction effect has been released, the reduced pressure applied can be decreased, so that the slug is not damaged.

Thereafter the carrier 24, and the holder 25 and punches 26 can be raised as indicated by the arrow Z in FIG. 6 (6).

Thereafter the carrier 24 is moved in the Y direction as illustrated in FIG. 6 (7) so that the punches are above a further Petri dish 56 including further agar 57. The carrier is then lowered as indicated by the arrow Z in FIG. 6 (8) to just above the upper surface of the agar 57 and the valve 49 closed and the valve 46 opened, so that the compressed air is introduced into the chambers in the punches and the slugs 58 are forced out onto the upper surface of the agar 57. Thereafter the carrier 24 is raised so that the punches move in the direction of the arrow Z in FIG. 6 (9) and the operation is then complete. If desired, the punches can then be lowered into a cleaning vessel by a suitable movement in the X or Y direction and in the Z direction.

By way of example, the hollow punches can be made of stainless steel and the holder 25 can also be made of stainless steel, with a stainless steel or polytetrafluoroethylene flange. The internal diameter of the hollow punches can vary within broad limits. However, it is necessary that the height of the core sample (slug) which is withdrawn should be greater than its radius. For example, the internal diameter of the hollow punch can be 4 mm for carrying out withdrawal of core samples, the height of which will be in the region of 4 mm. The useful height of the chamber 35 is preferably greater than the depth of the agar in the Petri vessel.

While FIG. 4 illustrates various possible constructions, best results have been found to be obtained when the lower portion of the hollow punch is bevelled outwards with a completely smooth wall (FIG. 4B). In general, the height of the bevelled portion is equal to or greater than the thickness of the agar from which the withdrawal is being made. The tubing 43 is preferably flexible, for example of silicon, and the negative pressure which can be produced by the vacuum source 52 is in the region of $-50$ mm hg while the compressed air preferably has an excess pressure of 100 mm hg.

The device, according to the invention can find application, e.g., in the selection of improved strains for producing an antibiotic or a growth factor, in the investigation of mutants which are overproductive of extracellular enzyme activity, or in the detection of new metabolites possessing therapeutic activity.

The examples which follow, which are given without implied limitation, illustrate the application of the device according to the invention.

EXAMPLE 1

Selection of Improved Strains

By means of the device which forms the subject of the invention, core samples are withdrawn from an agar nutrient medium, present in a Petri dish, on which the microorganism *Streptomyces ambofaciens,* a producer of spiramycin, is cultured.

The core samples are deposited on Petri dishes containing an agar medium seeded in its bulk with spores of *Bacillus subtilis,* which is a spiramycin-sensitive microorganism.

The spiramycin present in the core samples diffuses into the medium. After incubation at 37° C. to enable confluent growth of the test microorganism *Bacillus subtilis* to be obtained, rings of growth inhibition caused by spiramycin are observed around the core samples.

The existence of a linear relationship between the square of the diameter of the ring and the logarithm of the spiramycin concentration in the core sample enables the production of different strains to be compared, and the overproductive or non-productive mutant strains to be identified.

EXAMPLE 2

Investigation of Mutants Which Are Overproductive in Extracellular Enzyme Activity By means of the device which forms the subject of the present invention, core samples are withdrawn which are deposited at the surface of a medium containing the substrate for a specified enzyme.

A suitable test enables the possible degradation of the substrate around the core sample to be demonstrated. For example, in the case of cellulases produced by various microorganisms such as *Trichoderma reesei* or *Clostridium thermocellum,* the presence of the enzyme is shown by the appearance of a clear zone around the core sample due to the degradation of the cellulose which opacifies the medium.

EXAMPLE 3

Detection of New Metabolites Having Therapeutic Activity

Suitable dilutions of aqueous suspensions of natural samples (soils, marine sediments, etc.) are plated on sterile nutrient agar plates in Petri dishes.

These dishes are incubated at a suitable temperature until sufficiently well-developed and well-isolated microbial colonies are obtained.

The colonies selected for the experiments are withdrawn and transferred in an ordered fashion to fresh nutrient agar plates in Petri dishes.

After incubation at a suitable temperature, core samples are withdrawn by means of the device which forms the subject of the present invention, and are deposited on various test media for demonstration of the therapeutic activities sought.

For example, for the investigation of new antibiotics, the core samples can be deposited on media seeded with the microorganisms *Staphylococcus aureus* 209 P, *Escherichia coli* ATCC 9637, *Bacillus subtilis* ATCC 6633 or *Candida tropicalis.*

We claim:

1. A device for automatically carrying out the withdrawal and deposition of core samples of semi-solid media, said device comprising:
   (a) a carrier;
   (b) three separate guide means extending in three mutually perpendicular directions and mounting said carrier and guiding said carrier for accurate reciprocable movement in said three mutually perpendicular directions in a controlled manner;
   (c) a holder mounted on said carrier;
   (d) at least one hollow punch mounted on said holder, said at least one punch defining, in its interior, a punch chamber having a lower bevelled cutting edge;
   (e) a bore through said punch, communicating with said chamber, the diameter of said bore being less than the diameter of said chamber;
   (f) a compressed air source;
   (g) a vacuum generator;
   (h) means selectively connecting said bore to said compressed air source or said vacuum generator; and
   (i) control means governing the movement of said carrier and of said selecitve means, whereby the hollow punch may be raised from the bottom of the receptacle, and immediately thereafter carryout a horizontal shift in two mutually perpendicular directions, enabling air to penetrate under the core sample.

2. A device as claimed in claim 1 wherein said control means enable the following successive steps to be performed:
   (i) positioning of said at least one punch above a semi-solid medium from which the withdrawal is to be carried out;
   (ii) the descent and penetration of the punch to a depth in the region of 1 mm into the semi-solid medium and creation of a reduced pressure inside the hollow puhch by connection to the vacuum generator;
   (iii) descent of the hollow punch until it comes into contact with the bottom of the receptacle containing a certain scmi-solid medium;
   (iv) said raising of the hollow punch from the bottom of the receptacle, carrying out a horizontal shift In two mutually perpendicular directions, to enable air to penetrate under the core sample;
   (v) raising the hollow punch to the surface of the semi-solid medium and disconnecting the vacuum generator;
   (vi) raising of the hollow punch;
   (vii) positioning of the hollow punch above a medium on which the core sample is to be deposited;
   (viii) descent of the hollow punch to a distance above the semi-solid medium and connection to the compressed air generator;
   (ix) bringing the core sample into contact with the surface of the semi-solid medium under the action of compressed air and subsequently shutting off the compressed air;
   (x) slowly raising of the hollow punch, the core sample remaining in place on the semi-solid medium until the hollow punch is fully discharged.

3. A device according to claim 1, in which said at least one hollow punch is bevelled above its lower edge towards the outside of the chamber.

4. A device as claimed in claim 1, in which the hollow punch is bevelled at its lower portion towards the outside of the chamber and provided with at least one axial or helix groove along its exterior surface.

5. A device as claimed in claim 1 in which the hollow punch is bevelled from the lower edge on the inside of the chamber.

* * * * *